(12) United States Patent
Namiki

(10) Patent No.: US 7,079,232 B2
(45) Date of Patent: Jul. 18, 2006

(54) FOCUS DETECTING UNIT, AND REFRACTIVE INDEX MEASURING APPARATUS AND NON-CONTACT THERMOMETER USING THE SAME

(75) Inventor: Mitsuru Namiki, Hanno (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 10/945,098

(22) Filed: Sep. 21, 2004

(65) Prior Publication Data

US 2005/0062958 A1 Mar. 24, 2005

(30) Foreign Application Priority Data

Sep. 22, 2003 (JP) ............................... 2003-330210

(51) Int. Cl.
*G01N 21/41* (2006.01)
*G01N 21/00* (2006.01)
(52) U.S. Cl. ...................................... 356/128; 356/73.1
(58) Field of Classification Search ................ 359/738; 356/128, 129, 73.1
See application file for complete search history.

(56) References Cited

U.S. PATENT DOCUMENTS 4,441,811 A 4/1984 Melezoglu et al.
6,549,276 B1 4/2003 Longtin

FOREIGN PATENT DOCUMENTS

| EP | 0 994 341 A1 | 4/2000 |
| JP | 62-088929 | 4/1987 |
| JP | 2000-028526 | 1/2000 |

*Primary Examiner*—Ricky Mack
*Assistant Examiner*—Jack Dinh
(74) *Attorney, Agent, or Firm*—Kenyon & Kenyon LLP

(57) ABSTRACT

The focus detecting unit includes, a light source unit emanating a collimated light, an optical unit to be inspected, which is equipped with a container having translucency, a lens and liquid, a deflection unit which irradiates a light to the unit to be inspected by diffracting a light from the light source, a spot position detecting means 4 arranged near a backside focus plane of the optical unit to be inspected, and an operating means which calculates the composite focal length of a lens and liquid in the optical unit to be inspected by using the spot position detected by the spot position detecting means.

7 Claims, 11 Drawing Sheets

FIG.2
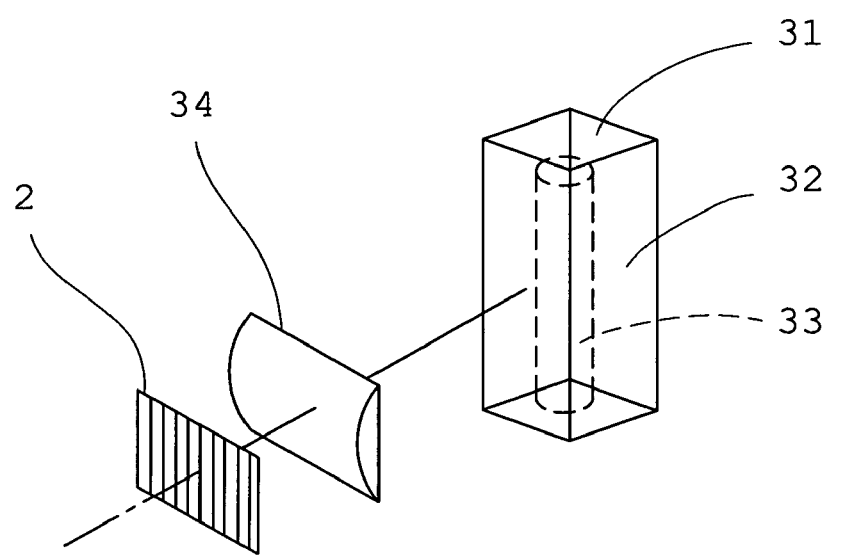
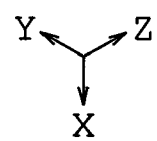

31  330  32

31  35  32

FIG.8A
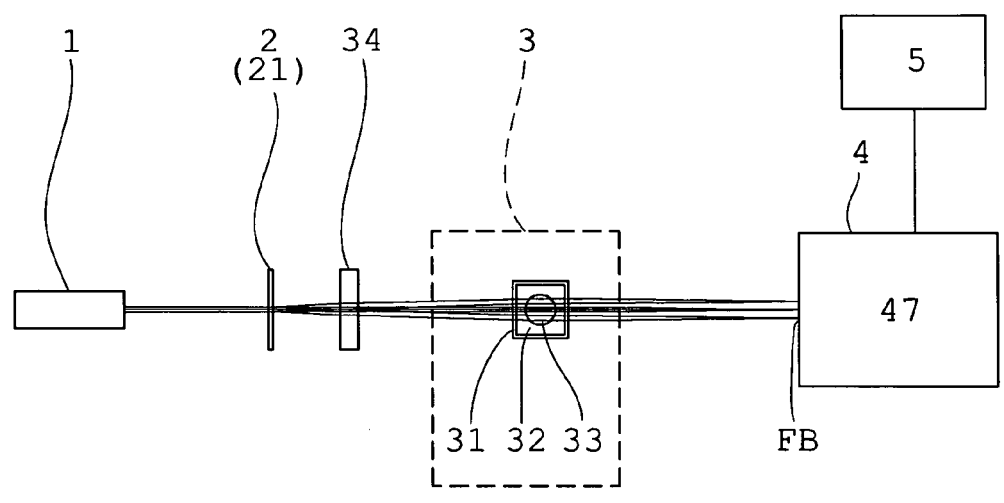
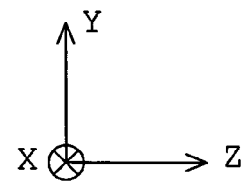
FIG.8B
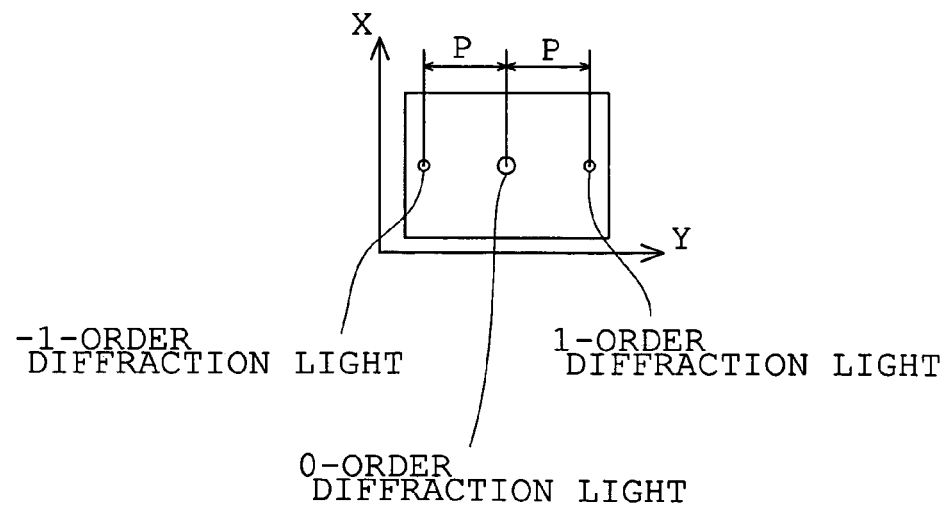
-1-ORDER DIFFRACTION LIGHT
1-ORDER DIFFRACTION LIGHT
0-ORDER DIFFRACTION LIGHT

FOCUS DETECTING UNIT, AND REFRACTIVE INDEX MEASURING APPARATUS AND NON-CONTACT THERMOMETER USING THE SAME

This application claims priority to Japanese Patent Application No. 2003-330210 filed 22 Sep. 2003, the content of which is incorporated herein by reference in its entirety.

BACKGROUND OF THE INVENTION

1. Field of the Invention

The present invention relates to a focus detecting unit, and a refractive index measuring apparatus and a non-contact thermometer using the same.

2. Description of the Related Art

As a conventional refractive index measuring apparatus, it has been proposed, for example, in Publication of Unexamined Patent Application of Japan, Toku Kai No. 2000-28526.

As a conventional non-contact type thermometer, it has been proposed in Publication of Examined Patent Application of Japan, Toku Kou Hei 5-66976.

That is, a refractive index measuring apparatus for liquid using an Arrayed Waveguide Grating type wavelength multiplexer-demultiplexer (hereafter, it is abbreviated as AWG) is shown in the publication of Toku Kai No. 2000-28526.

In this refractive index measuring apparatus of liquid, the light from a light source 40 is detected as a main wavelength $\lambda_{C0}$ by a spectrum analyzer, when there is no liquid in a groove 30.

On the other hand, if the groove 30 is filled up with liquid, it is detected as a central wavelength $\lambda_{C1}$ since phase modulation arises by an amount of the refractive index of the liquid.

The refractive index of the liquid filled in the groove can be calculated by determining the central wavelengths $\lambda_{C0}$, $\lambda_{C1}$ of a spectrum detected by this spectrum analyzer.

In a non-contact type thermometer disclosed in the Publication of Examined Patent Application of Japan, Toku Kou Hei 5-66976, an environmental temperature is measured. Here, facts that a quartz substrate on which a diffraction grating is formed is deformed by thermal expansion, and accordingly a lattice constant of the diffraction grating changes are utilized.

SUMMARY OF THE INVENTION

A focus detecting unit according to the present invention comprises, a light source unit emanating a collimated light, an optical unit to be inspected, having a transparent container in which a space holding an optical component and liquid is formed, a deflection unit which has a diffraction optical component and is arranged between the light source and the optical unit to be inspected, a spot position detecting means which is arranged near a backside focus plane of the optical unit to be inspected, and an operating means which calculates the composite focal length of a lens and liquid in the optical unit to be inspected by using the spot position detected by the spot position detecting means.

A refractive index measuring apparatus according to the present invention comprises, the focus detecting unit, and a refractive index calculating means for calculating one of unknown refractive indexes of the optical element and the liquid, wherein the refractive index calculating means calculates unknown refractive index from the composite focal length and one of known refractive index of the optical element or the liquid.

A non-contact thermometer according to the present invention comprises, the focus detecting unit, a temperature calculating means, wherein the temperature calculating means calculates an ambient temperature around the optical unit to be inspected from the composite focal length, the refractive index of the optical element and the refractive index of the liquid.

These features and advantages of the present invention will become apparent from the following detailed description of the preferred embodiments when taken in conjunction with the accompanying drawings.

BRIEF DESCRIPTION OF THE DRAWINGS

FIG. 2 is a partial perspective diagram of the focus detecting unit of the first embodiment 1.

FIG. 8 is a schematic block diagram of a focus detecting unit in the second embodiment according to the present invention.

DETAILED DESCRIPTION OF THE PREFERRED EMBODIMENTS

Figure 1:
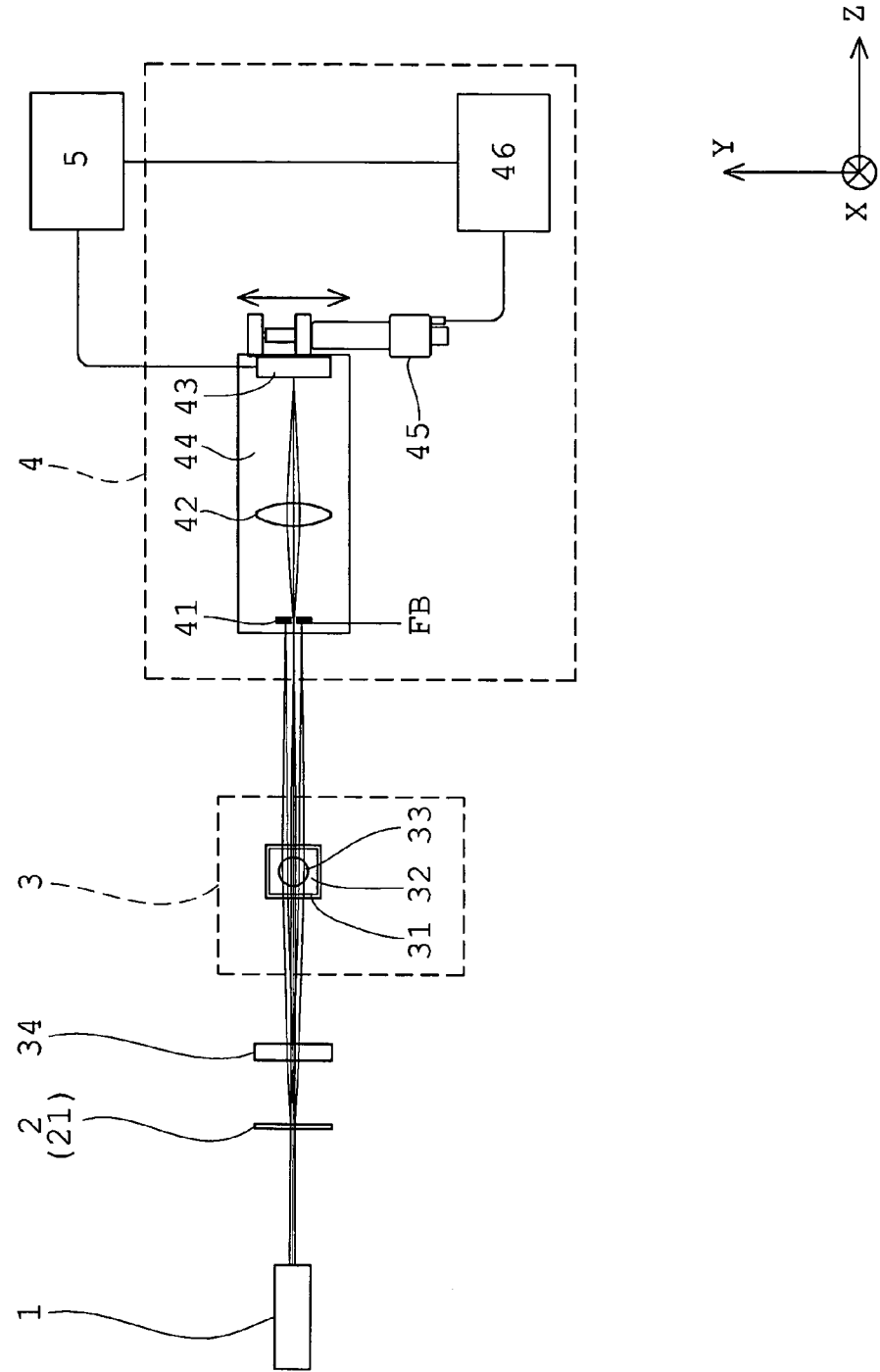
FIG. 1 is a schematic block diagram of a focus detecting unit in the first embodiment according to the present invention.

First, prior to explaining embodiments, reasons why the constitution of the present invention has been made as well as function and advantages according to the present invention will be explained.

If composed like the focus detecting unit according to the present invention, the composite focal length of an optical unit to be inspected or the focal length of an optical element can be easily determined with sufficient accuracy.

According to the present invention, a highly precise measurement of a refractive index can be carried out by incorporating a refractive index calculating means in an operating means.

Moreover, a highly precise non-contact measurement of temperature can be carried out by incorporating a temperature calculating means.

An highly precise measurement of refractive index and a non-contact temperature measurement can be simply carried out by switching using one focus detecting unit.

Moreover, if composed like the present invention, it is not necessary to use a conventional AWG and a spectrum analyzer which have been needed in a refractive index measurement.

Therefore, if composed like the present invention, the cost in cases of carrying out a refractive index measurement and a non-contact temperature measurement can be reduced remarkably.

In a refractive index measurement apparatus using the focus detecting unit according to the present invention, an irradiation unit diffracts a collimated light from a light source and irradiates it an optical unit to be inspected. Thus, a refractive index measurement of a wide wavelength range (from a visible region to telecommunication wavelength band) becomes possible since a wavelength range to be used is not limited as in a conventional AWG.

Moreover, in a non-contact type thermometer using the focus detecting unit according to the present invention, an ambient temperature of an optical unit to be inspected can be calculated from the composite focal length of the optical unit to be inspected, the refractive index of an optical element and the refractive index of liquid.

In the technique of a conventional technology (Japanese Examined Patent Publication Toku Kou Hei No. 5-66976), a fact that the lattice constant of a diffraction grating changes with the thermal expansion of a quartz substrate is utilized. However, the thermal expansion coefficient of quartz substrate is very small, which is about $4 \times 10^{-5}$. Therefore, a ratio of ΔP that is an amount of change by the temperature change at a spot position P is minute, that is, at most about $4 \times 10^{-5}$.

In the non-contact type thermometer of the present invention using an optical unit to be inspected, which contains liquid, the rate of temperature change at the focal length of the inspected optical unit which contains liquid becomes large about 10 to 100 times, comparing with a case where it does not contain liquid. Detail will be mentioned later. Since the change of a spot position is proportional to the focal length, it is possible to calculate a temperature with high precision that is 10 to 100 times or more as compared with a conventional technique.

Hereafter, embodiments of the present invention will be explained using drawings.

The First Embodiment

FIG. 1 is a schematic block diagram of a focus detecting unit in the first embodiment according to the present invention. FIG. 2 is a partial perspective diagram of a focus detecting unit of the first embodiment.

A focus detecting unit of the first embodiment has a light source 1 which emanates a parallel luminous flux, a deflection unit 2 which consists of diffraction gratings 21, a cylindrical lens 34, an optical unit 3 to be inspected, a spot position detecting means 4, and an operating means 5.

The diffraction grating 21 is arranged so that an incident luminous flux may be diffracted in a direction of y.

The optical unit 3 to be inspected has a glass cell 31, as shown in FIG. 2. The glass cell 31 is composed such that liquid 32 can be filled up and a rod lens 33 can be arranged in it.

In the example of FIG. 2, the rod lens 33 has optical power only in the direction of y. For this composition, in this embodiment, a cylindrical lens 34 which has power in a direction X is arranged in an optical path. By such composition, a light emanated from the inspected optical unit 3 is condensed and forms a spot light.

The spot position detecting means 4 is arranged near a backside focus plane FB of the inspected optical unit 3. Moreover, it has a pinhole 41, a lens 42, a photoelectric element 43, a stage 44, an automatic drive element 45, and a control device 46. The pinhole 41 is arranged near the backside focus plane FB. The stage 44 holds the pinhole 41, the lens 42 and the photoelectric element 43. An automatic drive element 45 moves the stage 44 in the direction (direction of an arrow as indicated) perpendicular to the optical axis. A control device 46 controls a drive of the automatic drive element 45. In such composition, the collimated light irradiated to the inspected optical unit 3 penetrates the inspected optical unit 3. Then, this light forms a spot on the photoelectric element 43 through the pinhole 41 and the lens 42. Thus, a spot position can be detected by the spot position detecting means 4.

The operating means 5 is composed such that a composite focal length of the rod lens 33 and the liquid 32 can be calculated. In this calculation, the spot position detected through the spot position detecting means 4 is used.

Figure 3:
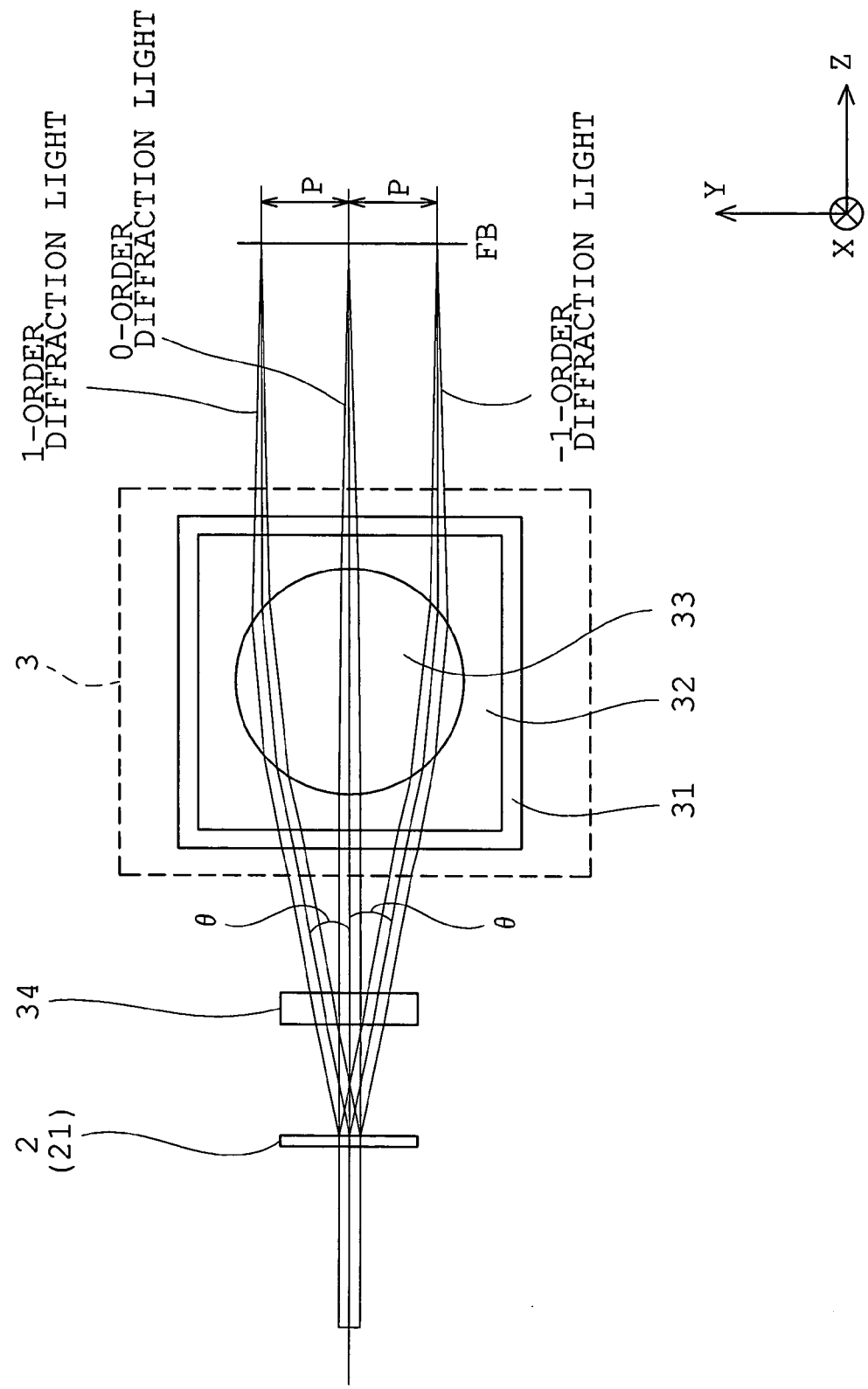
FIG. 3 is a drawing for explaining a principle of measuring the composite focal length of the optical unit to be inspected in the focus detecting unit of the first embodiment.

Next, by using FIG. 3 the principle of measurements of the composite focal length of the inspected optical unit 3 will be explained.

In this embodiment, the deflection unit 2 is composed of the diffraction grating 21. When a parallel luminous flux emanated from the light source 1 enters into the diffraction grating 21, two or more diffracted lights generate in the direction of y. In FIG. 3, 0-order light and ±1-order diffracted light are only shown for convenience sake.

Each diffracted light is condensed near the backside focus plane FB through the inspected optical unit 3. As mentioned above, in the example of FIG. 3, the inspected optical unit 3 has power only in the direction of y. Therefore, as a cylindrical lens 34, a lens having power in the x directions is used.

Figure 4:
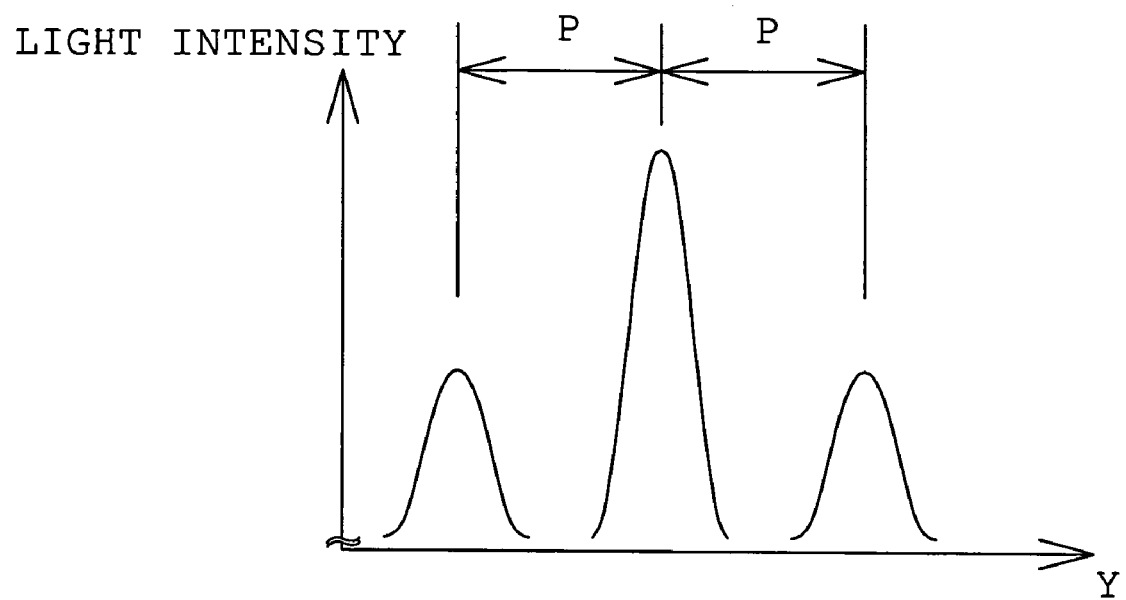
FIG. 4 is a graph showing distribution of the intensity of light to a spot position of each diffracting light near the backside-focus-plane FB of an optical unit to be inspected in the focus detecting unit of the first embodiment.

As a result, the spot of each diffracted light is generated near the backside focus plane FB. FIG. 4 is a graph showing a distribution of the intensity of light to the spot position of each diffracted light. This spot position is near the backside focus plane FB of the inspected optical unit 3. In FIG. 4, p shows an interval between the spot of 0-order diffracted light, and the spot of ±1 order diffracted light.

Next, a method how to find the composite focal length of the inspected optical unit 3 from the spot interval p of each diffracted light will be explained. Calculation of the composite focal length is carried out via the operating means 5.

The diffraction angle θ which is formed by 0-order diffracted light and ±1-order diffracted light can be expressed by the following equation (1), where s represents the spatial frequency of the diffraction grating, and λ represents the wavelength of the light emanated from the light source 1.

$$\theta = \sin^{-1} s\lambda \tag{1}$$

The spot interval p which is an interval between ±1-order diffracted light and 0-order diffracted light (hereafter it is abbreviated as the distance p.) can be expressed by the following equation (2), where reference symbol f represents the composite focal length of the optical unit 3 to be inspected.

$$p = f \tan \theta \quad (2)$$

That is, by determining the spot position of ±1-order diffracted light, the composite focal length of the optical unit 3 to be inspected can be calculated easily from the equation (2).

Figure 5:
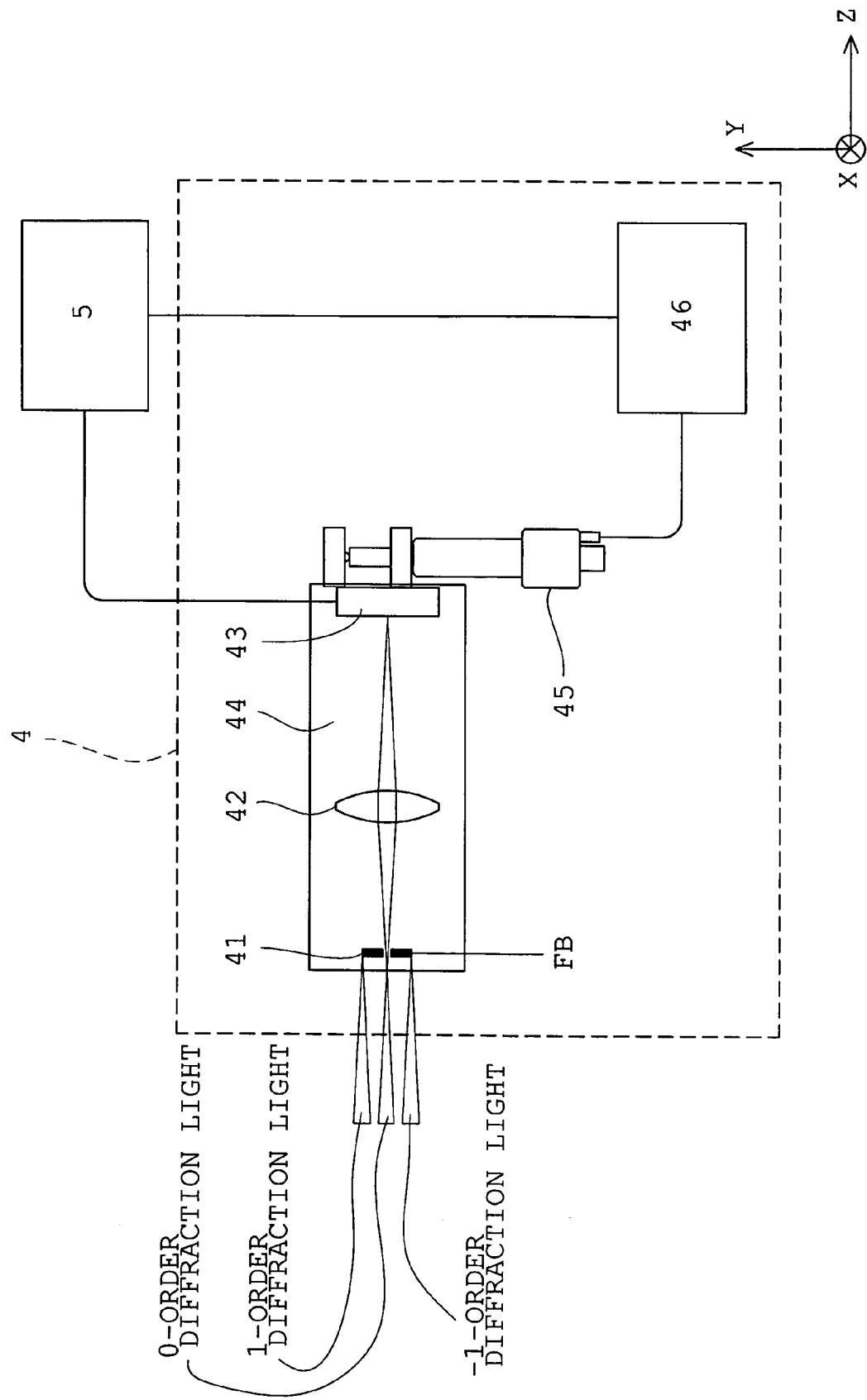
FIG. 5 is a drawing showing elements on larger scale of the spot position detecting means of FIG. 1.

Next, measurement of the spot position of each diffracted light by the spot position detecting means 4 is explained using FIG. 5.

FIG. 5 is a partial diagram of elements on larger scale of the spot position detecting means 4 in FIG. 1.

A pinhole 41, a lens 42 and a photoelectric element 43 are fixed on the stage 44. An automatic drive element 45 is driven through a control device 46. By this composition, the pinhole 41, the lens 42 and the photoelectric element 43 can be moved to the direction of y simultaneously.

The pinhole 41 and the photoelectric element 43 have a conjugate relation to the lens 42. Thus, the light penetrating the pinhole 41 is received by the photoelectric element 43. By this way, the intensity of light in the pinhole 41 position is detected by the photoelectric element 43. FIG. 5 shows a state where 0-order diffracted light is detected.

By the automatic drive element 45, the stage 44 is moved in the direction (here, to the direction of y) perpendicular to the optical axis sequentially. Then, the intensity of the light which has penetrated the pinhole 41 is measured at each spot position. Then, as shown in FIG. 4, a graph showing an optical intensity to an amount of stage movement (spot position) is obtained. The interval p in FIG. 4 shows the spot interval between 0-order diffracted light and ±1-order diffracted light as mentioned above.

Next, the refractive index measuring apparatus using the focus detecting unit of this embodiment (hereafter, it is abbreviated as the refractive index specifying unit) is described. As mentioned above, in the operating means 5, the composite focal length of the optical unit 3 to be inspected can be obtained. Then, a calculation processing means (program) to calculate the refractive index of the rod lens 33 or the liquid 32 from the composite focal length of this optical unit 3 to be inspected is provided. Thus, a composition having a function as a refractive index measuring apparatus can be realized.

This calculation processing means is a refractive index calculating means. This calculation processing means is independent from the operating means 5. However, this can be a part of the operating means 5. This refractive index measuring means, that is, a process for calculating the refractive index of the rod lens 33 or the refractive index of the liquid 32 using the composite focal length of the optical unit 3 to be inspected will be explained.

Figure 6:
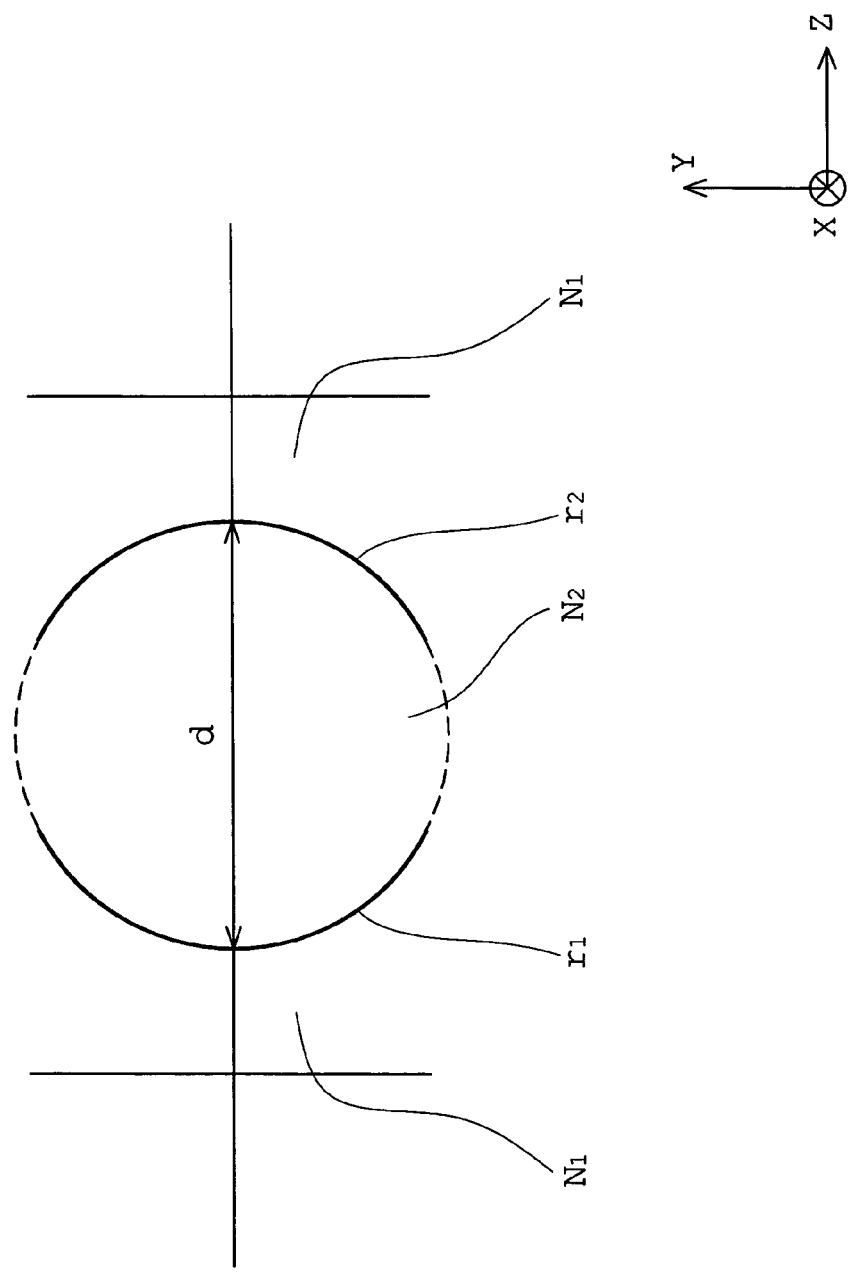
FIG. 6 is a diagram for explaining a calculation of the composite focal length of an optical unit.

The glass cell 31 of the inspected optical unit 3 is formed by sticking parallel plates, which has no optical power. For this, the composite focal length of the inspected optical unit 3 is determined by the shape and the refractive index of the rod lens 33, and the refractive index of the liquid 32 only. Then, calculation of the composite focal length of the optical unit 3 will be explained by using FIG. 6. Here, the glass cell 31 is formed by a parallel plate, and it has no optical power. Therefore, here it is ignored since it hardly contributes to the composite focal length.

When $N_1$ represents a refractive index of the liquid, and $r_1$, $r_2$, $d$ and $N_2$ represent a radius of curvature of the first surface of the rod lens 33, a radius of curvature of the second surface, a distance between surfaces and the refractive index respectively, the composite focal length f of the optical unit 3 to be inspected can be expressed by the following equation (3).

$$\frac{1}{f} = (N_2 - N_1)\left(\frac{1}{r_1} - \frac{1}{r_2}\right) + \frac{(N_2 - N_1)^2}{r_1 r_2}\frac{d}{N_2} \quad (3)$$

If this equation (3) is solved about the refractive index $N_1$ of the liquid 32, or about the refractive index $N_2$ of the rod lens 33, they can be expressed by the following equation (4), (5.1) and (5.2), respectively. Therefore, when the refractive index $N_1$ of the liquid 32 is unknown, it will become possible to calculate the refractive index from the equation (4) if values other than $N_1$ have been determined in the equation (3). When the index of the refraction N2 of the rod lens 33 is unknown, it will become possible to calculate the refractive index from the following equations (5.1) and (5.2) if values other than N2 have been determined respectively.

$$N_1 = N_2 - \frac{-b + \sqrt{b^2 - 4ac}}{2a} \quad (4)$$

$$a = \frac{d}{N_2 r_1 r_2}$$

$$b = \left(\frac{1}{r_1} - \frac{1}{r_2}\right)$$

$$c = -\frac{1}{f}$$

$$N_2 = \frac{-B + \sqrt{B^2 - 4AC}}{2A} \quad A \neq 0 \quad (5.1)$$

$$N_2 = -\frac{C}{B} \quad A = 0 \quad (5.2)$$

$$A = \frac{d}{r_1 r_2} + \frac{1}{r_1} - \frac{1}{r_2}$$

$$B = -N_1\left(\frac{1}{r_1} - \frac{1}{r_2}\right) - \frac{2N_1 d}{r_1 r_2} - \frac{1}{f}$$

$$C = \frac{N_1^2 d}{r_1 r_2}$$

A result determined according to this technique for the refractive index of water and the refractive index of glass will be shown.

First, explanation for determining the refractive index of water will be given.

In the light source unit 1, a light source which emanates light with the wavelength of 632.8 nm is arranged. Thus, a collimated light with the wavelength of 632.8 nm is emanated from the light source 1 with the wavelength of 632.8 nm. A deflection means 2 is a diffraction optical component. Concretely, it is composed of a diffraction grating having a grid spacing of 10 grid/mm. At this time, the diffraction angle of 0-order diffracted light is 0.363°.

Silica glass was used as a glass cell 31. A rod lens 33 is a commercially available rod lens. Specifically, it has the radii of curvature $r_1 = 2.499$ mm and $r_2 = -2.499$ mm, the surface distance $d = 4.998$ mm, and refractive index $N_2 = 1.51509$. Water ($N_1 = 1.33174$) was used for the liquid 32.

A stage 44 is moved by an automatic drive element 45. At this time, a width of moving step is set to 0.1 micrometers, and then a stage 44 is moved. Then, the intensity of light of each diffracted light as shown in FIG. 4 can be obtained. Then, computing according to the equation (2) is carried out by the operating means 5. As a result, the composite focal length f of the inspected optical unit 3 was f=7.739±0.0056 mm. The refractive index of the water was 1.3317±0.00013, when it was calculated by the equation (4) based on this composite focal length. This result is very close to the value of 1.33174 shown in a reference.

When assuming that the refractive index of glass of the rod lens 33 was unknown, the refractive index of the glass of the rod lens 33 was determined from f=7.739±0.0056 mm and equation (5). As a result, it was determined as 1.51505±0.00020. This is very close to the value of 1.51509 shown in a catalog.

As mentioned above, the refractive index measuring apparatus of this embodiment is provided with a refractive index calculating means of this technique in the focus detecting unit of this embodiment. According to this refractive index measuring apparatus, it is possible to measure a refractive index of a lens or liquid correctly.

Moreover, in this refractive index measuring apparatus, there is no limits of a wavelength range to be used as seen in AWG of a conventional example. Thus, according to this refractive index measuring apparatus, refractive index measurement over a wide range of wavelength spectrum (from a visible band to communication wavelength band region) can be attained only by changing the light source unit 1. Furthermore, in case a refractive index is measured, there is no necessity for lens processing in which V shape groove is formed in AWG in the refractive index measuring apparatus of the conventional example.

Moreover, according to this refractive index measuring apparatus, low-pricing can be realized, as compared with the refractive index measuring apparatus of the conventional example since an expensive optical element or optical instrument, such as AWG and a spectrum analyzer, are not needed.

Figure 7A:
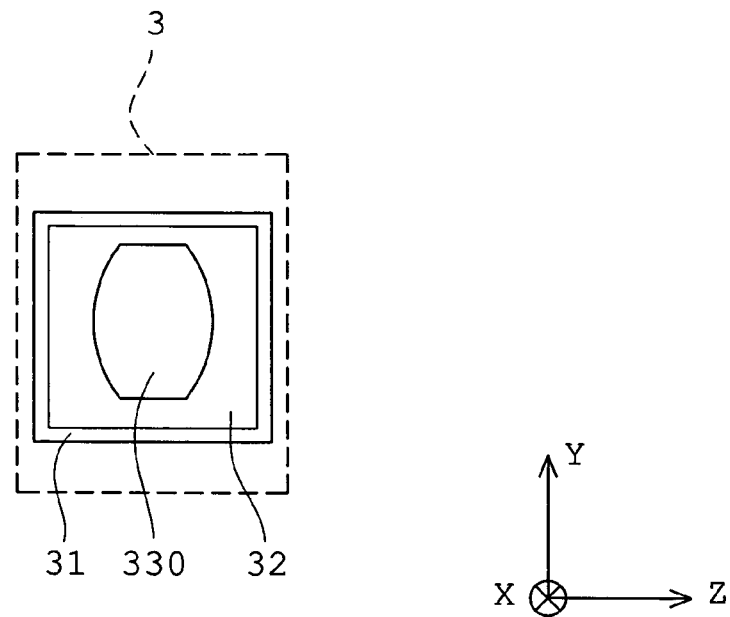
FIGS. 7A and 7B are a top view and a side view of modified examples of an optical unit to be inspected in the focus detecting unit of the first embodiment.
Figure 7B:
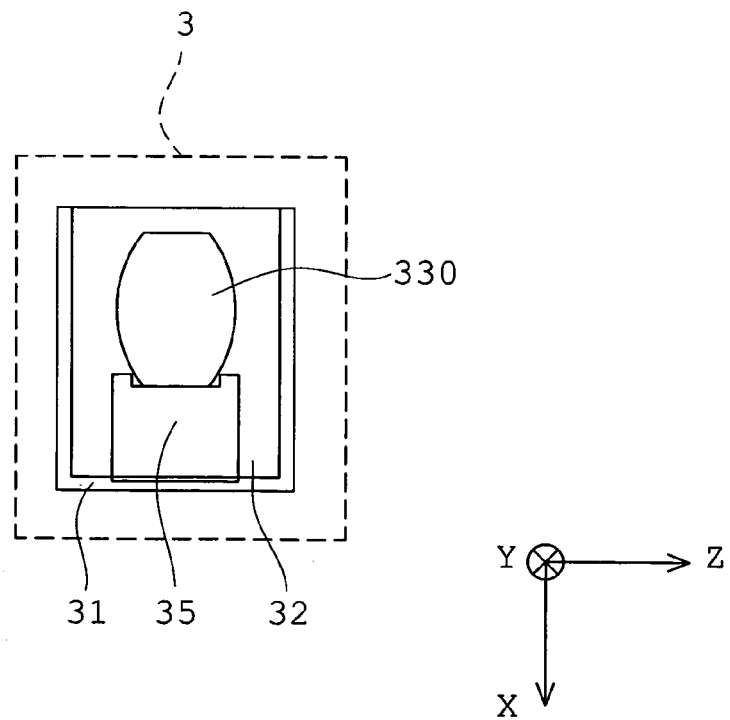

Although the rod lens 33 is used in this embodiment, it may be the lens 330 which is symmetrical with rotation as shown in FIGS. 7A and 7B. In this case, the lens 330 is arranged in a glass cell using a maintenance jig 35. Also in this case, it becomes possible to measure the refractive index of the lens 330 or the liquid 32 as shown in the case using the rod lens 33. In this case, the light from the inspected unit 3 forms a spot light since the lens 330 has power in the x and y directions. Thus, the cylindrical lens 34 becomes unnecessary.

Moreover, in focal length measurement of a lens, when a focal length is short, there is a problem that accuracy falls. Consequently, when the focal length is short, it is difficult to calculate the refractive index of the lens from measurement of the focal length. However, the composite focal length of the inspected optical unit 3 can be made longer than the focal length of the rod lens 33 or the lens 330 by itself by soaking in the liquid 32 as shown in the first embodiment.

If the focal length of the rod lens 33 or the lens 330 is long, the glass cell 31 and the liquid 32 are not needed. In this case, a refractive index can be calculated by measuring directly a focal length of a lens.

The Second Embodiment

FIG. 8 is a schematic block diagram of a focus detecting unit in the second embodiment of the present invention.

The second embodiment is a modified example of the first embodiment and uses an imaging element 47 as a spot position detecting means 4. If the imaging element 47 is arranged near a backside focus plane FB of the inspected optical unit 3, a spot pattern shown in FIG. 8B can be obtained. An operating means 5 is composed such that it calculates the composite focal length of the inspected optical unit 3 by determining a spot interval p from the coordinate of spot of each of this diffracted light. The refractive index calculation processing after the composite focal length calculation is the same as that of the first embodiment.

It is desirable to use CCD, CMOS sensor, etc. as an imaging element 47. The spot position detecting means 4 may be PSD (position detecting element). In that case, it is good enough to have a composition which irradiates a spot sequentially on PSD one by one.

The Third Embodiment

Figure 9:
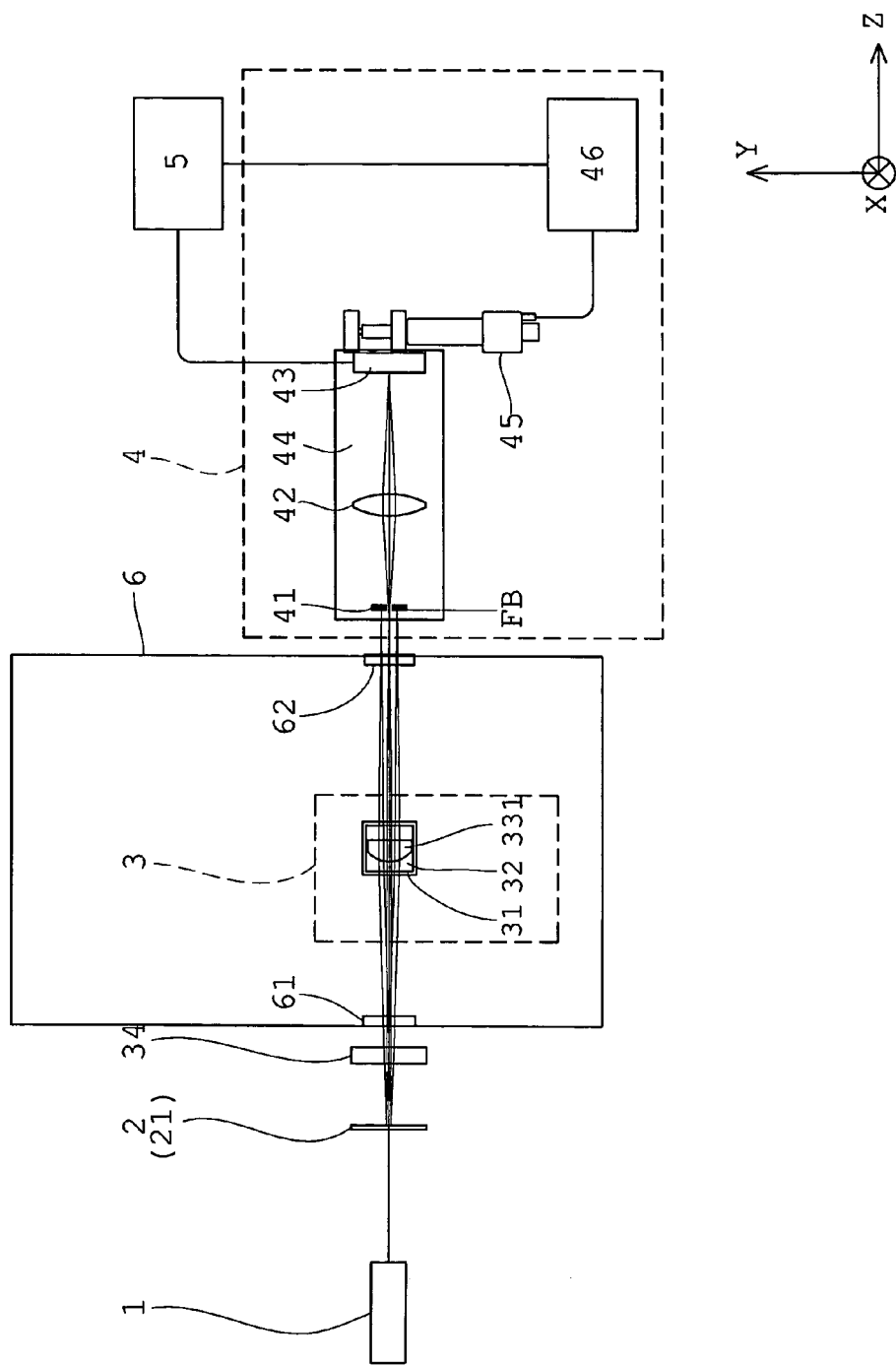
FIG. 9 is a schematic block diagram of a non-contact type thermometer using a focus detecting unit in the third embodiment according to the present invention.

FIG. 9 is a schematic block diagram of a non-contact type thermometer using the focus detecting unit in the third embodiment according to the present invention.

A non-contact type thermometer of the third embodiment includes a light source 1 which outputs a parallel luminous flux, a deflection unit 2 which is composed of a diffraction gratings 21, an optical unit 3 to be inspected, a spot position detecting means 4 and an operating means 5.

The optical unit 3 to be inspected is composed such that inside of a glass cell 31 can be filled up with liquid 32. Furthermore, it is composed such that a lens 331 and a maintenance jig (illustration is omitted: equivalent to the maintenance jig 35 in FIG. 7) holding the lens 331 can be arranged.

A spot position detecting means 4 has a pinhole 41, a lens 42, a photoelectric element 43, a stage 44, an automatic drive element 45, and a control device 46. The pinhole 41 is arranged near a backside focus plane FB of the inspected optical unit 3. The stage 44 holds the pinhole 41, the lens 42 and the photoelectric element 43. The automatic drive element 45 moves the stage 44 in the direction perpendicular to the optical axis. The control device 46 controls the automatic drive element 45.

In the third embodiment, it is assumed that the radius of curvature, the distance between the surfaces and the refractive index of the glass cell 31, the lens 331 and the liquid 32 are known all. It is assumed that the temperature dependency concerning the refractive index of the liquid 32 also is known.

The inspected optical unit 3 is arranged in an environment 6 in which an internal temperature is measured. The environment 6 has penetrable parallel plates 61 and 62 in which light can be guided.

Moreover, a temperature calculating means is provided as the operating means 5. Here, the temperature calculating means is arranged independently from the operating means 5. By this temperature calculating means, the temperature in the environment 6 is determined using the composite focal length of the optical unit to be inspected. The temperature calculating means can be built in the operating means 5.

Next, a procedure for non-contact measuring the temperature of inside of the environmental 6 using a temperature calculation processing means will be shown, where it is assumed that all of the components in the environment 6 are at the same temperature.

Figure 10:
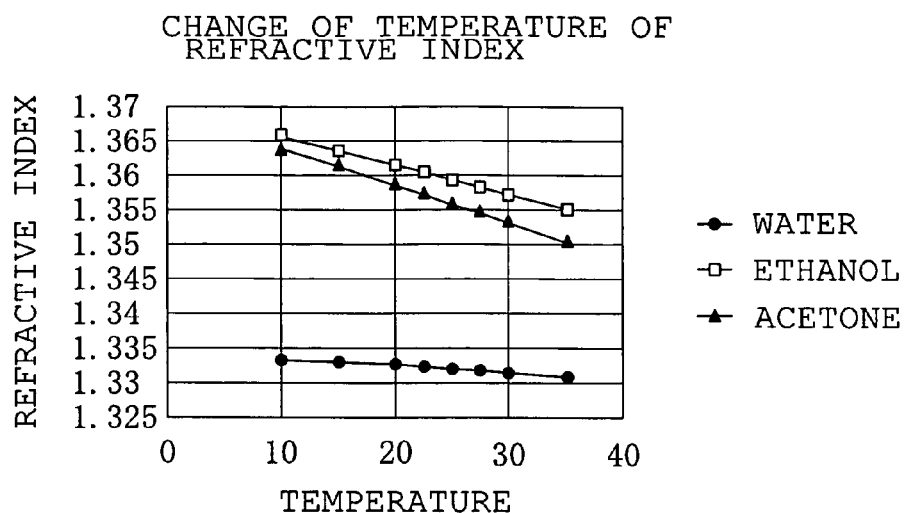
FIG. 10 is a graph showing changes of refractive indexes to the temperature of liquid which are water, ethanol or acetone, used for an optical element to be inspected in the second embodiment.

Generally, the rate of temperature change to the refractive index of glass is about $10^{-6}$, while that of liquid is large nearly two figures to that of glass. The temperature changes of the refractive index of water, ethanol and acetone are shown in FIG. 10. Here, the wavelength of light source is 589.3 nm.

If it is assumed that each refractive index varies approximately linearly to temperature, the rate of the temperature change to each refractive index will be $1\times10^{-4}$ for water, $4\times10^{-4}$ for ethanol and $5.4\times10^{-4}$ for acetone.

Here, the temperature change to the refractive index of glass is disregarded since it is small compared with that of liquid. The refractive index of the liquid 32 at temperature T is defined as N2(T). Then, the composite focal length f(T) of the inspected optical unit 3 in FIG. 9 can be expressed in the following equation (3T) according to the equation (3).

$$\frac{1}{f(T)} = (N_2 - N_1(T))\left(\frac{1}{r_1} - \frac{1}{r_2}\right) + \frac{(N_2 - N_1(T))^2}{r_1 r_2}\frac{d}{N_2} \quad (3T)$$

In FIG. 10, it is assumed that acetone which has the largest rate of change of refractive index by temperature change is used as liquid 32. Then, the composite focal length of the inspected optical unit 3 is determined from the equation (3T). The values of the equation (3T) are shown below, where the refractive index is the value at the wavelength of 589.3 nm.

$r_1$=31.11 mm
$r_2$=∞
d=2.05 mm
$N_1(T)$=−5.4188×$10^{-4T}$+1.3694
$N_2(T)$=1.51626

Figure 11:
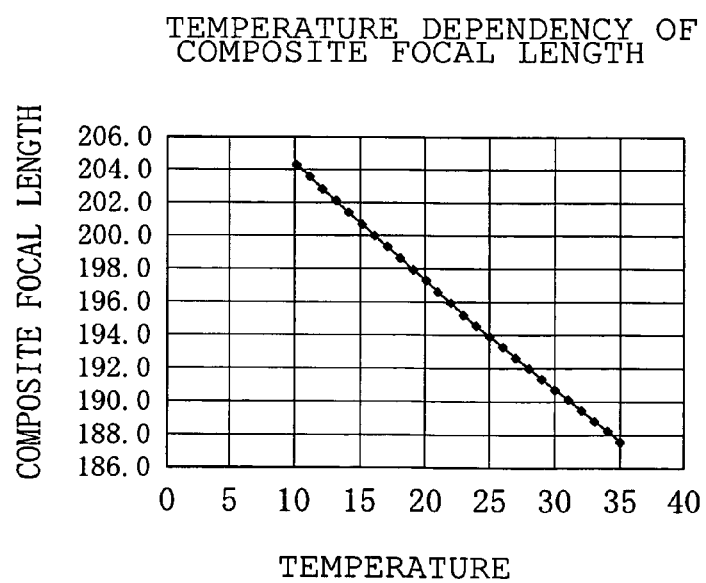
FIG. 11 is a graph showing change of the composite focal length to the temperature of an optical unit to be inspected in the focus detecting unit of the second embodiment.
Figure 12:
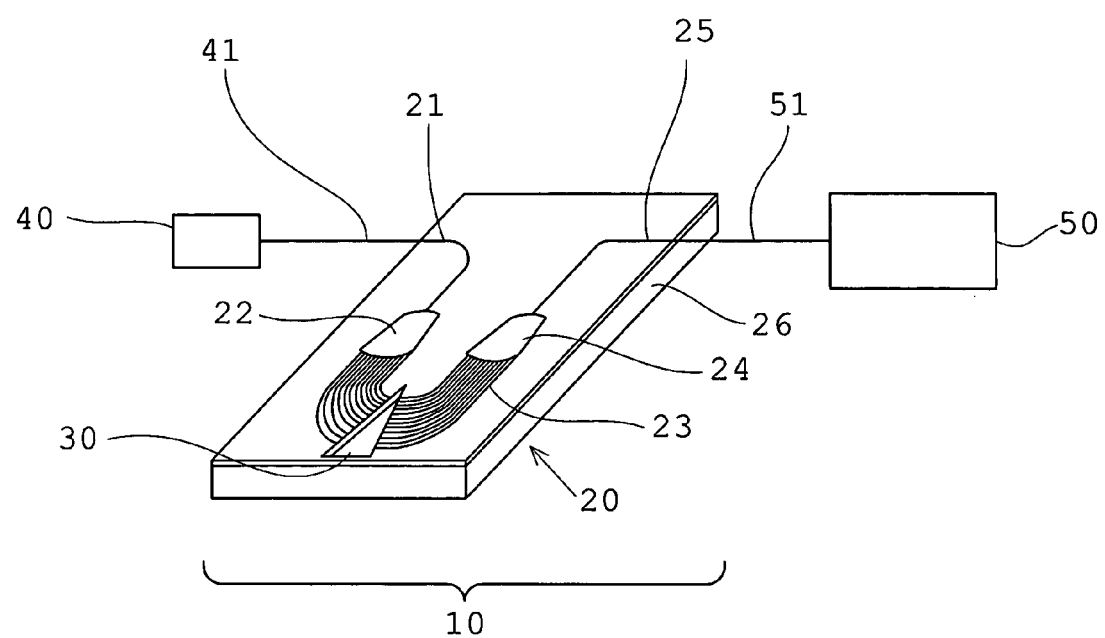
FIG. 12 is a schematic block diagram showing one of conventional examples of a refractive index measuring apparatus.

If the values mentioned above are applied to the equation (3T) in order to determine the temperature change of the composite focal length of the optical unit 3 to be inspected, it becomes as shown in FIG. 11. When the focal length at the temperature of 20° C. is based, it is seen that change by +3.5% at 10° C. and change by −5% at 35° C. occur.

Then, as shown in FIG. 9, the optical unit 3 to be inspected is installed in the environment 6 in which the temperature is measured, and the composite focal length is determined. In this way, it becomes possible to determine the temperature of the inside of the environment 6 from the graph of FIG. 10. Moreover, the graph of FIG. 10 is regarded as linear, and it is approximated by a primary equation. Thus, a relational expression like the following equation (6) is obtained. Then, it is also possible to determine a temperature T by applying the value of the composite focal length of the inspected optical unit 3 to the following equation (6).

$$f(T) = -0.6672T + 210.74 \quad (6)$$

Next, a measurement accuracy of temperature will be explained. The measurement accuracy of temperature is determined by the measurement accuracy of the composite focal length of the inspected optical unit 3. Then, first of all, the measurement accuracy of the composite focal length will be explained.

In FIG. 9, the measurement accuracy of the composite focal length can be estimated from the ratio of the spot interval between 0-order diffracted light and ±1-order diffracted light, and the step width of the automatic drive element 45 of the spot position detecting means 4. If an error of measurement of the interval p is set to Δp, an error of measurement Δf(T) of the composite focal length f(T) can be expressed by the following equation (2') from the equation (2).

$$\Delta f(T) = \Delta p / \tan\theta \quad (2')$$

The relation between the error of measurement Δf(T) of the composite focal length and the error of temperature ΔT is obtained from the equation (6) as follows.

$$\Delta T = -\Delta f(T)/0.6672 \quad (6')$$

It is considered that the error-of-measurement Δp of the interval p in the spot position detecting means 4 is comparable as the step width of the automatic drive element 45. Since a stage having step width about 0.1 micrometers is available recently in a commercial market, it is set as Δp=0.1 μm. Furthermore, as to the light source of wavelength λ of the light source 1, it is set as λ=589.3 nm and a spatial frequency of the diffraction grating 21 is set to 10 lines/mm. Thus, a value of ΔT=0.023° C. is be obtained from the equations (2') and (6').

The measurement accuracy of temperature in a conventional example is about 5° C. Therefore, according to the non-contact type thermometer using the focus detecting apparatus of the third embodiment, it can be seen that the accuracy of 200 times or more than that of the conventional example can be attained.

As the spot position detecting means 4, it is possible to use the imaging element 47 as shown in the second embodiment.

It is also possible to incorporate selectively the focus detecting unit with the refractive index calculation processing means or temperature calculation processing means in each of embodiments mentioned above. It is also possible to incorporate selectively the refractive index calculation processing means and the temperature calculation processing means with the operating unit, in the focus detecting unit of each of embodiments mentioned above. In this way, it becomes possible to carry out simply switching of refractive index measurement and non-contact temperature measurement by using one focus detecting unit.

According to the present invention, the composite focal length of a unit which is composed of an optical element such as a lens and the like and liquid can be easily obtained with sufficient accuracy. Moreover, by combining a focus detecting unit with an refractive index calculation processing or a temperature calculation processing, it becomes possible to carry out simply switching of refractive index measurement and non-contact temperature measurement with high accuracy. Furthermore, by composing a focus detecting unit like that of the present invention, it is not necessary to use AWG and a spectrum analyzer which have been needed conventionally in refractive index measurement. Therefore, if composed like the focus detecting unit according to the present invention, the cost for performing an refractive index measurement and a non-contact temperature measurement can be reduced greatly.

Furthermore, according to the refractive index measuring apparatus using the focus detecting unit according to the present invention, the irradiation means which irradiates the collimated light from the light source to the optical unit to be inspected does not limit wavelength range used, which is different from the conventional AWG, where usable wavelength is limited. Thus, a refractive index measurement of a wide range of wavelength (a visible region-communication wavelength band) becomes possible.

Moreover, according to the non-contact type temperature measuring apparatus using the focus detecting unit according to the present invention, an ambient temperature of the optical unit to be inspected can be calculated from the composite focal length of the optical unit to be inspected. Therefore, the temperature can be calculated with high precision by 10 to 100 or more times in comparison to the conventional case where temperature is calculated from the focal length of glass, of which a rate of temperature change is small.

What is claimed is:

1. A focus detecting unit comprising,
   a light source unit emanating a collimated light
   an optical unit to be inspected, having a transparent container in which a space holding an optical element and liquid is formed,
   a deflection unit having a diffraction optical component, arranged between the light source and the optical unit to be inspected,
   a spot position detecting means arranged near a backside focus plane of the optical unit to be inspected, and
   an operating means which calculates a composite focal length of the optical element and liquid in the optical unit to be inspected using the spot position detected by the spot position detecting means.

2. The focus detecting unit according to claim 1, wherein the diffraction optical component has 1-dimensional periodic structure.

3. The focus detecting unit according to claim 2, wherein the spot position detecting means has a moving mechanism, and the moving mechanism moves the pinhole, the lens, and the light detecting device.

4. The focus detecting unit according to claim 1, wherein the spot position detecting means has a pinhole, a lens and a light detecting device, and the pinhole, the lens and the light detecting device are arranged so that the pinhole and the light detecting device are in a conjugated relationship.

5. The focus detecting unit according to claim 1, wherein the spot detecting unit has a light detecting device, and the light detecting device has a property enabling to detect the position of an incident light by itself.

6. A refractive index measuring apparatus comprising, the focus detecting unit according to claim 1, and
   a refractive index calculating means which calculates one of unknown refractive indexes of the optical element and the liquid,
   wherein the refractive index calculating means calculates the unknown refractive index from the composite focal length and one of the known refractive indexes of the optical element or the liquid.

7. A non-contact thermometer comprising, the focus detecting unit according to claim 1, and
   a temperature calculating means,
   wherein the temperature calculating means calculates an ambient temperature around an optical unit to be inspected from the composite focal length, the refractive index of the optical element and the refractive index of the liquid.

* * * * *